US008519005B2

(12) United States Patent
Thomas

(10) Patent No.: US 8,519,005 B2
(45) Date of Patent: Aug. 27, 2013

(54) COMPOSITIONS AND METHODS TO PREVENT TOXICITY OF ANTIINFLAMMATORY AGENTS AND ENHANCE THEIR EFFICACY

(76) Inventor: Thomas N. Thomas, Palm Harbor, FL (US)

( * ) Notice: Subject to any disclaimer, the term of this patent is extended or adjusted under 35 U.S.C. 154(b) by 1227 days.

(21) Appl. No.: 10/802,000

(22) Filed: Mar. 16, 2004

(65) Prior Publication Data
US 2004/0176469 A1 Sep. 9, 2004

Related U.S. Application Data

(63) Continuation-in-part of application No. 10/061,734, filed on Feb. 1, 2002, now abandoned, and a continuation-in-part of application No. 09/881,199, filed on Jul. 27, 2000, now Pat. No. 6,432,991, and a continuation-in-part of application No. 10/137,342, filed on May 3, 2002, now Pat. No. 6,635,667.

(51) Int. Cl.
*A61K 31/135* (2006.01)
(52) U.S. Cl.
USPC ............ 514/652; 514/646; 514/649; 514/651
(58) Field of Classification Search
USPC .................. 514/649, 646, 651, 652
See application file for complete search history.

(56) References Cited

U.S. PATENT DOCUMENTS

| | | | |
|---|---|---|---|
| 5,916,910 A * | 6/1999 | Lai ............................. | 514/423 |
| 6,432,991 B1 | 8/2002 | Thomas | |
| 6,482,846 B1 | 11/2002 | Garvey et al. | |
| 6,544,556 B1 | 4/2003 | Chen et al. | |
| 6,593,347 B2 | 7/2003 | Bandarage et al. | |
| 6,613,784 B1 | 9/2003 | Benedini et al. | |
| 6,635,667 B2 | 10/2003 | Thomas | |
| 6,649,629 B2 | 11/2003 | Bandarage et al. | |

OTHER PUBLICATIONS

Linaping et al., Monoamine Oxidase B Inhibition Reduces Gastric Mucosal Blood Flow, Basal Acid Secretion and Cold Water Restraint-Induced Gastric Mucosal Injury in Rats, Digestive Diseases and Sciences, vol. 35 No. 1 Jan. 1990 pp. 61-65.*
http://www.merck.com/mmpe/sec02/ch013/ch013a.html accessed Jan. 4, 2009.*
http://www.medicinenet.com/script/main/art.asp?articlekey=43451 accessed Mar. 17, 2010.*
Lauer MS. Aspirin for primary prevention of coronary events. N Engl J Med, 346: 1468-1474, 2002.
Fennerty BM. NSAID-related gastrointeitinal injury. Postgraduate Medicine, 110: 87-94, 2001.
Yeomans ND. Approaches to healing and prophylaxis of nonsteroidal antiinflammatory Drug-associated ulcers. Am. J. Medicine. 110/1A:24S-28S.
GlavinGB, et al. L-deprenyl attennuates stress ulcer formation in rats. Neurosci. Letters. 70: 379-381 (1986).
ThyagaRajan S. Anti-tumor effect of l-deprenyl—in rats with carcinogen-induced Mammary tumors. J. Neuroimmunol. 109: 95-104, 2000.
Thomas, T; et al. L-Deprenyl: nitric oxide productionand dilation of cerebral blood vessels. NeuroReport, 9:1-6, 1998.
Thomas,T. Monoamine oxidase-B inhibitors in the treatment of Alzheimer's disease. Neurobiol. Aging. 21:343-348, 2000.
Thomas T,et al. Aspirin and diabites: inhibition of amylin aggregation by nonsteroidal Antiinflammatory drugs. Exp Clin Endocrinol Diabetes. 111: 8-11, 2003.
Thomas, T. et al. Inhibition of LDL oxidation by the neuroprotective drug I-deprenyl. Neurol. Res. 24:169-173, 2002.
Wallace JL and Soldato DL. The therapeutic potential of NO-NSAIDS. Fundamental & Clin Pharmacol. 17: 11-20, 2003.
Fiorucci, S. "Prevention of nonsteroidal anti-inflammatory drug-induced ulcer: looking to the future." Gastroenterol Clin North Am. Jun. 2009;38(2):315-32.
Wikipedia definition of Aspirin. http://en.wikipedia.org/wiki/Aspirin, accessed Mar. 6, 2012.
Fiorucci, S. Prevention of Nonsteroidal Anti-Inflammatory Drug-Induced Ulcer: Looking to the Future. Gastroenterol Clin N Am, 38:315-332, 2009.
Sigma-Aldrich product information for Propargylamine. http://sigmaaldrich.com/catalog/ProductDetail.do? D7=0 &N5=SEARCH_CONCAT . . . , accessed Mar. 6, 2012.
Wikipedia definition of Selegiline. http://en.wikipedia.org/wiki/Selegiline, accessed Mar. 6, 2012.

* cited by examiner

*Primary Examiner* — My-Chau T Tran
(74) *Attorney, Agent, or Firm* — Robert J. Varkonyi; Smith & Hopen, P.A.

(57) ABSTRACT

Effects of deprenyl or propargylamine compounds (MAO inhibitors) and novel compositions comprising at least one MAO inhibitor and at least one antiinflammatory agent such as nonsteroidal antiinflammatory drugs (NSAIDS), steroids, acetaminophen (COX-3 inhibitors), 5-lipoxygenase inhibitors, leukotriene receptor antagonists, leukotriene A4 hydrolase inhibitors, antihistaminics, histamine 2 receptor antagonists, phosphodiesterase-4 antagonists, cytokine antagonists, CD44 antagonists, antineoplastic agents, 3-hydroxy-3-methylglutaryl coenzyme A inhibitors (statins), estrogens, androgens, antiplatelet agents, antidepressants, *Helicobacter pylori* inhibitors, proton pump inhibitors, thiazolidinediones, dual-action compounds, combinations of these drugs with other agents, derivatives and metabolites of synthetic and natural antiinflammatory agents. The compounds and compositions protect against gastrointestinal, renal and other toxicities induced by antiinflammatory agents, and enhance the beneficial effects of these drugs. Effects of MAO inhibitors such as 1-deprenyl co-administered with antiinflammatory drugs or chemically attached to antniinflammatory drugs are disclosed. Therapeutic methods of using MAO inhibitors and antiinflammatory drugs for the prevention and treatment of inflammatory disorders, pain, fever, cancer, gastrointestinal lesions, and a variety of cardiac, cerebral and peripheral disorders are disclosed.

6 Claims, No Drawings

COMPOSITIONS AND METHODS TO PREVENT TOXICITY OF ANTIINFLAMMATORY AGENTS AND ENHANCE THEIR EFFICACY

RELATED APPLICATION

This is a continuation-in-part of U.S. application Ser. No. 10/061,734, filed Feb. 1, 2002, now abandoned; U.S. application Ser. No. 09/881,199 filed Jul. 27, 2000, entitled Methods of Treatment using MAO-A and MAO-B Inhibitors such as L-Deprenyl, now U.S. Pat. No. 6,432,991; and U.S. application Ser. No. 10/137,342, filed May 3, 2002, entitled Methods of Treatment using MAO-A and MAO-B Inhibitors such as L-Deprenyl, now U.S. Pat. No. 6,635,667.

FIELD OF THE INVENTION

This invention relates to the field of antiinflammatory drugs and compositions that prevent reduce or reverse the gastrointestinal, renal and other toxicities associated with antiinflammatory agents, and at the same time provide additional tissue protection.

STATEMENT REGARDING FEDERAL SPONSORED R & D

No federal, state, or other government funding was used to develop this patent.

BACKGROUND OF THE INVENTION

The major causes of physical disability (arthritis, osteoporosis, stroke, lupus, inflammatory bowel disease, asthma, allergy), mental deterioration (Alzheimer's disease, Vascular dementia, depression, Parkinson's disease), and death (cardiovascular disease, diabetes, cancer), all are initiated and propagated by systemic inflammation (Brod 2000; Thomas 2003). Under normal conditions inflammation is a response to injury and has a major role in immune function and tissue repair. A dysregulation of the inflammatory mechanism may occur with aging or infection, and the influence of environmental and genetic factors. Mediators of inflammation such as C-reactive protein, cytokines, adhesion molecules, and metaloptoteinases may also contribute to the development and progression of inflammatory processes. Thus reduction of levels of inflammatory markers may indicate amelioration of the inflammatory process and reduced risk for inflammatory diseases. A number of antiinflammatory drugs are currently used and new agents are being developed for the prevention and treatment of inflammatory disorders. Antiinflammatory agents are the most widely used class of medications world-wide. The major drugs with antiinflammatory action are nonsteroidal antiinflammatory drugs (NSAIDS), steroids, acetaminophen (COX-3 inhibitors), 5-lipoxygenase inhibitors, leukotriene receptor antagonists, leukotriene A4 hydrolase inhibitors, angiotensin converting enzyme antagonists, beta blockers, antihistaminics, histamine 2 receptor antagonists, phosphodiesterase-4 antagonists, cytokine antagonists, CD44 antagonists, antineoplastic agents, 3-hydroxy-3-methylglutaryl coenzyme A inhibitors (statins), estrogens, androgens, antiplatelet agents, antidepressants, *Helicobacter pylori inhibitors* , proton pump inhibitors, thiazolidinediones, dual-action compounds, combinations of these drugs with other agents, derivatives and metabolites of synthetic and natural antiinflammatory agents. Nonsteroidal Antiinflammatory Drugs (NSAIDS)

NSAIDS are a group of drugs that, despite significant differences in their chemical structure and pharmacological profile, share common activities such as antiinflammatory, analgesic, antipyretic and antiplatelet actions. The NSAIDS are the most widely consumed drugs worldwide, with an estimated 50-60 million individuals in the United States alone using them on a regular basis. Novel actions of aspirin and other NSAIDS are increasing the number of individuals using these compounds. NSAIDS are increasingly being used for the prevention and/or treatment of arthritis, inflammation, gout, pain, fever, and cardiovascular disease, complications of diabetes, stroke, cancer, Alzheimer's disease and dementia (Patrono, 2001; Gupta 2001, In'T Veld, 2001). An aspirin resistance syndrome has been described in some patients taking aspirin (Hankey, 2004). NSAIDS also provide protection against degenerative diseases by reducing the production, aggregation and deposition of amyloidogenic proteins like amyloid-beta, and amylin (Thomas, 2001, 2003)

Even though NSAIDS have several biological actions, their major beneficial effects are considered to be mediated through the inhibition of the enzyme cyclooxygenase (COX) responsible for conversion of arachidonic acid to prostaglandins. Cyclooxygenase exists in two unique isoforms encoded by separate genes and exhibits distinct patterns of tissue-specific expression. COX-1 is primarily expressed constitutively and functions as a physiologic "housekeeping enzyme" in most tissues including gastric mucosa, the kidneys and platelets. COX-2 expression, especially in macrophages and synovial cells is induced by inflammatory stimulus (Emery, 2001). Commonly used NSAIDS inhibit both COX-1 and COX-2 enzymes to varying degrees. But recent evidence indicates that COX 2 is also constitutively expressed in many tissues (Hennan et al., 2000) and the inhibition of COX-2 may induce endothelial dysfunction. The therapeutic benefits of conventional NSAIDS are believed to be derived from the inhibition of COX-2, while the adverse effects, particularly gastrointestinal toxicity, occur as a result of their effects on COX-1. This has led to the development of a new class of compounds, which selectively inhibits COX-2 only and may have a reduced level of gastrointestinal side effects compared to conventional NSAIDS.

NSAID Toxicity

Despite impressive therapeutic benefits, NSAID use places individuals at a risk for several serious complications such as gastrointestinal (GI) toxicity, renal damage and platelet dysfunction (Fennerty, 2001; Gramlich, 2001; Rocha et al, 2001). The major complication is gastrointestinal toxicity, which has a wide array of clinical manifestations ranging from dyspeptic symptoms to life-threatening intestinal bleeding or perforation of gastro duodenal mucosa and gastric outlet obstruction (Wolfe et al; 1999). The gastrointestinal toxicity is evident even at low doses of aspirin used for prevention of myocardial infarction. In fact NSAID toxicity is considered to be the number one cause of drug-induced complications. NSAID-related ulcer complications lead to up to 400,000 hospitalizations and 16,500 deaths yearly in the United States. Concomitant administration of other NSAIDS along with aspirin also reduces the anti-platelet and cardiovascular benefits of aspirin by interfering with cyclooxygenase inhibition (Catella-Lawson, 2001).

The toxic effects of NSAIDS may be mediated by reduced gastric mucosal blood flow, neutrophil adhesion, free radical generation, and reduced mucous secretion as shown below.

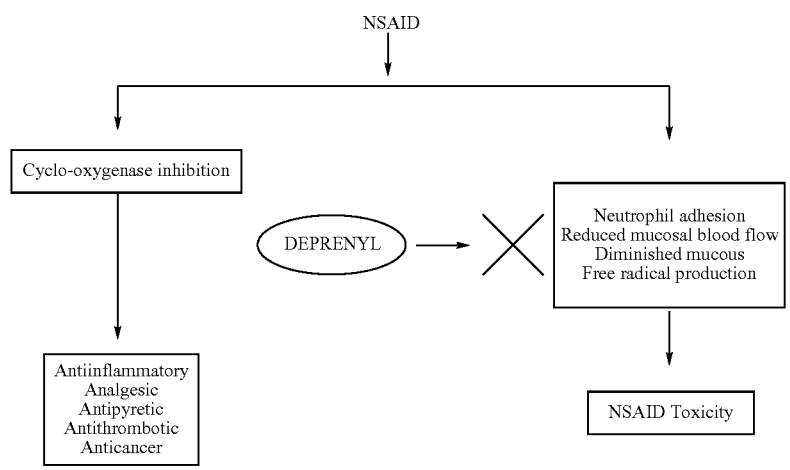

NSAID-induced gastropathy involves topical irritant effects on the epithelium as well as the deleterious effects of inhibition of prostaglandin synthesis. Loss of prostaglandin-mediated protection makes the gastric mucosa susceptible to damage induced by acid or other irritants. The effects of NSAID on gastric microcirculation is considered to be the most important factor leading to mucosal injury (Wallace 2003). NSAIDS reduce gastric mucosal blood flow through endothelial damage, neutrophil adhesion, liberation of oxygen radicals and capillary obstruction.

Deprenyl and related compounds have the ability to prevent NSAID-induced gastric damage through enhancing blood flow, prevention of neutrophil adhesion, reducing free radical toxicity, endothelial protection, stimulation of antioxidant enzymes, and antiinflammatory actions.

Several strategies have been employed to reduce the gastrointestinal toxicity caused by NSAIDS (Lanas, 2001). These include enteric coating to prevent absorption in the stomach, parental administration, use of pro-drugs that require hepatic metabolism to produce cyclooxygenase inhibition, co administration of gastro protective agents (proton pump inhibitors, histamine-2 receptor antagonists, prostaglandins), COX-2 specific drugs, and nitric oxide releasing NSAIDS (Wallace, 1999; 2003; Yeomans, 2001). All of these methods have significant limitations and have not significantly reduced the incidence or complications of NSAID toxicity. For example COX-2 inhibitors are not devoid of GI toxicity, may cause hypertension and edema, and do not inhibit platelet thromboxane production. In addition COX-2 derived prostacyclin has important cardioprotective effects and inhibition of this activity may increase the risk of acute vascular events in patients receiving these drugs (Hennan 2000, Mukherjee 2001). The nitric oxide releasing NSAIDS produce only local effects. The nitric oxide is released locally in the stomach and has short half-life of less than 30 seconds. Therefore it will not provide long periods of protection and also will not prevent the toxic effect of NSAIDS of other targets such as the kidney. Thus there is an urgent need to develop new methods to prevent, reduce or reverse NSAID toxicity.

COX-3 Inhibitors

The COX-3 inhibitor acetaminophen (Tylenol) is widely used analgesic and antipyretic drug. At high doses acetaminophen is toxic to liver, kidney, and other tissues. Acetaminophen may cause cell damage by stimulating apoptosis through mitochondrial damage, and generation of toxic oxygen radicals and peroxynitrite (James 2003; Boulares 2002).

Steroids

Glucocorticoids are agents used in a number of disorders like asthma, rheumatoid arthritis and psoriasis. This group includes short-acting agents (cortisone, hydrocortisone), intermediate-acting agents (prednisone, methylprednisone, triamcinolone), and long-acting agents (dexamethasone, betamethasone). Glucocorticoid use is associated with complications such as weight gain, hypertension, Cushingoid facies, diabetes mellitus, osteoporosis, myopathy, increased intraocular pressure, ischemic bone necrosis, infection, hypercholestolemia. exacerbation of peptic ulcer, gastritis and esophagitis.

Lipoxygenase Inhibitors

The metabolism of arachidonic acid by lipoxygenase pathway generates leukotrienes. Leukotrienes generated by 5-lipoxygenase activity are proinflammatory. They increase microvascular permeability, are potent chemotactic agents and attract eosinophils, neutrophils and monocytes to the inflammatory site (Lotzer 2003). 5-lipoxygenase inhibitors (eg. Licofelone) are being tested as antiinflammatory agents. These compounds have toxic effects on a number of tissues.

Leukotriene Modifiers

Leukotrienes formed by the 5-lipoxygenase pathway have a major role in altering the biology of airway wall in asthma. Leukotriene modifiers including leukotriene receptor antagonists, and leukotriene A4 hydrolase inhibitors, are currently used in the treatment of asthma. Examples of leukotriene receptor antagonists are montelukast, pranlukast, and zafirlukast. These drugs inhibit smooth-muscle constriction, eosinophil migration, and edema in airway.

Antihistamines

Allergic rhinitis is an inflammatory condition of the nose characterized by sneezing, rhinorrhea, and obstruction of nasal passages. Antihistamines like chlorpheniramine, astemizole, and loratidine are used to treat allergic rhnitis.

Phosphodiesterase Inhibitors

Type 4 phosphodiesterases (PDE4) belong to a superfamily of at least 11 isoenzymes catalyzing the hydrolysis of second messengers cyclic AMP and/or cyclic GMP. PDE4 regulates the intracellular levels of cyclic AMP and are the major PDE expressed in inflammatory cells (Jacob 2002, Zhu 2001). The vide range of inflammatory mechanisms regulated by PDE4 makes this enzyme an attractive target for antiinflammatory drugs. PDE4 inhibitors have been shown to be effective in the treatment of chronic inflammatory diseases like asthma, chronic obstructive pulmonary disease (COPD), rheumatoid arthritis, cancer, hepatitis, autoimmune disease, brain inflammation, and endogenous depression.

PDE4 inhibitors have behavioral and other side effects like nausea and emesis.

Statins

Statins (HMG-CoA reductase inhibitors) are widely used to lower lipid levels and accord protection against cardiovascular disease. Recent evidence indicates that some of the benefits of statins are due to non-lipid mechanisms. A major component of the pleiotropic effects of statins is considered to be due to their antiinflammatory action (Werner 2002). Most of the currently available statins have the potential to cause complications (Muscari 2002). The complications include altered liver function, skeletal muscle and peripheral nerve changes, flu-like symptoms, weakness, aching muscles and joints. The major side effect is myopathy, rhabdomyolysis and ensuing acute renal insufficiency.

Estrogens

Postmenopausal women have a higher incidence of inflammatory disorders including cardiovascular disease, arthritis, and Alzheimer's disease, possibly due to estrogen deficiency. A number of reports have indicated that the beneficial effects of estrogen may be partly due to antiintlammatory activity (Thomas, 2003).

But estrogen use is associated with a number of side effects. The adverse events include elevation of CRP level, increased cardiovascular events, stroke, thromboembolism, cancer, and dementia (Writing group for WHI, 2002).

Thiazolidinediones

Thiazolinediones like rosiglitazone and pioglitazone are used in the treatment of diabetes. The action of these drugs is partially mediated by their antiinflammatory action as they reduce the levels of several markers of inflammation including CRP.

Combination Drugs

Several dual acting and combination antiinflammatory drugs are currently in use, These include combinations of NSAIDS or other antiinflammatory agents with other drugs. Examples of such combination drugs include Aggrenox (aspirin+dipyridamole), Darvon (aspirin+propoxyphene+caffeine), Excedrin (aspirin+actaminphen+caffeine), Percodan (aspirin+oxycodone), Soma (aspirin+carisprodol), Synalogos (aspirin+dihydrocodeine+caffeine), Butabital (aspirin+caffeine+codeine), Norgesic (orphenadrine+caffeine), (see Physicians Desk Reference 2003, page 103 for complete list); aspirin+statins, aspirin+antioxidants, aspirin+vitamins, aspirin+steroid hormones, NSAID+5-lipoxygenase inhibitors, or NSAID+phosphodiesterase-4 inhibitors.

This invention relates to methods and compositions to ameliorate antiinflammatory drug toxicity by using inhibitors of monoamine oxidase (MAO) enzymes. Monoamine oxidases catalyze the deamination of monoamines. MAO exists in two different forms, MAO-A and MAO-B, encoded by two distinct gene loci, with different patterns of tissue distribution (Knoll et al; 1972, Shih 1991). MAO-A preferentially deaminates serotonin and is more sensitive to inhibition by clorgyline, whereas MAO-B preferentially deaminates β-phenylethylamine and is inhibited by drugs such as 1-deprenyl. The MAO-B inhibitor 1-deprenyl is effective in the treatment of Parkinson's disease, Alzheimer's disease and depression, and has been found to extend the life span (Knoll 1989, Birkmayer 1985).

It is now evident that the therapeutic efficacy of 1-deprenyl may involve cytoprotective actions other than the inhibition of MAO-B. These include a variety of biological actions such as neuroprotection, endothelial protection, anti-inflammatory activity, antioxidant action, free radical scavenging, antiapoptotic action, up-regulation of growth factors like NGF, BDNF, and GDNF (Mizuta 2000), reduction of hypoxia, reduction of oxidative stress, antagonism of cytotoxic actions of toxic agents such as amyloid-β peptide, inhibition of tumor growth, vasodilation, increased blood flow, inhibition cytochrome P450 enzymes (Dycek 2000) enhanced expression of antioxidant enzymes (Thomas 2000, Carillo 2000, Surronen 2000, Thyagarajan 2000) and stimulation of constitutive nitric oxide synthase enzymes resulting in the enhanced production of nitric oxide (Thomas 1998). A combination of these actions contributes to the ability of MAO inhibitors to ameliorate the toxic effects of NSAIDS and provide tissue protection (Galvin, 1986).

SUMMARY OF THE INVENTION

It is an object of the present invention to provide a method and compositions to prevent, reduce, and/or reverse the serious complications such as gastrointestinal toxicity, renal damage, mucosal damage, endothelial dysfunction, ischemia, and platelet dysfunction and other toxicities produced by antinflammatory drugs in animal, particularly a human and in addition provide additional tissue protection.

It is another object of the present invention to provide a method to prevent or reduce the side effects of COX-2 inhibitors such as gastrointestinal toxicity, renal damage, hypertension, edema, thrombosis, endothelial dysfunction, and increased cardiovascular events.

It is another object of the present invention to enhance the benefits of COX 2 inhibitors by endothelial and vascular function, inhibiting platelet aggregation, reducing inflammation, and inhibiting cancer growth.

It is a further object of the present invention to provide a method of co-administering a MAO inhibitor and antiinflammatory drug so that the resulting composition not only possess potent analgesic, anti-inflammatory and antipyretic properties but has much reduced potential for producing gastrointestinal, renal or other damage and provide tissue protection in an animal, particularly a human.

It is another object of the present invention to provide a method for the protection to tissues such as blood vessels, heart, and brain through the beneficial actions of MAO inhibitors co-administered with antiinflammatory drugs.

It is another object of the present invention to provide a method to enhance the antiinflammatory actions of NSAIDS glucocorticoids, statins, estrogens, and combinations of antiinflammatory drugs with other agents.

It is another object of the present invention to provide a method to reduce the side effects of NSAIDS (COX-1, COX-2), COX-3 inhibitors, 5-lpoxygenases inhibitors, phosphodiesterase inhibitors glucocorticoids, statins, estrogens, and combinations of antiinflammatory drugs with other agents through the beneficial actions of MAO inhibitors co-administered with antiinflammatory drugs It is another object of the present invention to provide a method for enhancing the antiplatelet activity of aspirin in patients with cardiovascular disease, stroke, or diabetes.

It is another object of the present invention to provide a method for preventing or treating cognitive dysfunction syndrome (dementia) in cats and dogs by administering antiinflammatory drugs along with MAO inhibitors.

It is yet another object of the present invention to provide a method of co administering a MAO inhibitor and through the beneficial actions of MAO inhibitors co-administered with antiinflammatory drugs so that the resulting compositions are effective in the treatment and/or prevention of arthritis, inflammation, pain, fever, gout, cardiovascular disease, diabetes, hypertension, stroke, ischemia, thromboembolism, cancer, head trauma, spinal trauma, multiple sclerosis, amyotrphic lateral sclerosis, fibromyalgia, Down's syndrome, Alzheimer's disease and dementia, but has a much reduced potential for producing toxic side effects.

It is a further object of the present invention to provide methods and compositions to enhance the effectiveness of through the beneficial actions of MAO inhibitors co-administered with antiinflammatory drugs by providing additional cytoprotective effects of MAO in the treatment of Parkinson's disease. Alzheimer's disease, depression, cardiovascular disease, diabetes, cancers and the extension of life span.

It is another object of the present invention to provide a composition comprising an through the beneficial actions of MAO inhibitors co-administered with antiinflammatory drug, which is directly or indirectly linked to a MAO inhibitor. The antiinflammatory drug can for example be a nonspecific cyclooxygenase inhibitor, or a selective COX-1, COX-2 or COX-3 inhibitor, glucocorticoid, lipoxygenase inhibitor, PDE4 inhibitor, statin, estrogen, or a combination.

It is another object of the invention to provide a method for preventing or reversing hypertension and other cardiovascular side effects of NSAIDS, particularly the COX-2 inhibitors by using MAO inhibitors.

It is a further object of the present invention to provide a method for preventing and/or treating gastrointestinal ulcers by administering a MAO inhibitor either alone or in combination with other agents (e.g. histamine-2 receptor antagonists, prostaglandins, proton pump inhibitors) used in the treatment of such ulcers.

It is another object of the present invention to provide a method for providing long-term protection lasting several hours, from the toxic effects of antiinflammatory drugs by administering MAO inhibitors.

It is a further object of the invention to provide a method for protecting the kidney and other tissues, in addition to the gastrointestinal tract from the toxic actions of antiinflammatory drugs through the beneficial actions of MAO inhibitors co-administered with antiinflammatory drugs by administering MAO inhibitors.

It is another object of the present invention to provide a method for preventing gastrointestinal and other toxicities of low dose aspirin and other NSAIDS through the beneficial actions of MAO inhibitors co-administered with antiinflammatory drugs used for the prevention of conditions such as cardiovascular disease and cancer by administering a MAO inhibitor along with these compounds.

It is another object of the present invention to provide a method for preventing, decreasing or reversing stress-induced ulcer by administering a MAO inhibitor alone or in combination with agents used in the treatment of such ulcers.

It is a further object of the present invention to provide a method for preventing and/or treating ulcers caused by alcohol, tobacco, drugs or microorganisms such as *Helicobacter Pylori* by administering a MAO inhibitor alone or in combination with agents used in the treatment of such ulcers.

It is another object of the present invention to provide a method for preventing NSAID toxicity and provide tissue protection by using MAO inhibitors when the NSAID is administered along with other drugs for the treatment of a number of conditions (e.g. NSAID administered with estrogens, acetylcholinesterase inhibitors, NMDA antagonists, statins, secretase inhibitors, or amyloid vaccines for the treatment of Alzheimer's disease; or aspirin, antiplatelet drugs or statins for the treatment of cardiovascular disease).

It is another object of the invention to provide a method for preventing or reversing gastrointestinal and other toxicities of through the beneficial actions of MAO inhibitors co-administered with antiintlammatory drugs from natural sources (e.g. aspirin-like compounds from willow bark) by coadministering MAO inhibitor along with these natural preparations.

It is a further object of the invention to provide a method for long-term use of antiinflammatory drugs through the beneficial actions of MAO inhibitors co-administered with antiinflammatory drugs for the relief of pain, inflammation, fever or other conditions.

The of MAO inhibitors co-administered with antiinflammatory drugs and MAO inhibitor can be administered separately or as an ingredient of the same preparation.

It is another object of the invention to provide a method for long-term use of through the beneficial actions of MAO inhibitors co-administered with antiinflammatory drugs for the prevention and treatment of degenerative diseases caused by the increased levels, aggregation or deposition of amyloidogenic proteins like amylod-beta. The antiinflammatory drugs and MAO inhibitor can be administered separately or as an ingredient of the same preparation.

It is a further object of the present invention to provide a method for reducing the levels of the inflammatory mediators like C-reactive protein and cytokines and provide protection against inflammatory disorders, cardiovascular disease and side effects of hormone replacement therapy by co-administering a antiinflammatory drug toxicity-reducing amount of a MAO inhibitor. The antiinflammatory drugs and MAO inhibitor can be administered separately or as an ingredient of the same preparation.

It is another object of the invention to prevent, decrease or reverse kidney disease induced by NSAID alone or in combination with other drugs such as phenacetin and caffeine in an animal, particularly human, by administering a MAO inhibitor.

It is a further object of the invention to preserve and enhance anti-platelet and cardiovascular benefits of aspirin, when aspirin is administered concomitantly with other NSAIDS, by administering a MAO inhibitor.

The compounds and compositions of the present invention are novel and will have utility in treating a number of degenerative disorders and disease states. For example, reperfusion injury to an ischemic organ, inflammatory bowel disease, rheumatoid arthritis, osteoarthritis, gout, hypertension, eclampsia, chronic renal failure, kidney disease, hepatitis, organ transplant rejections, organ preservation, radiation-induced injury, cancer, asthma, atherosclerosis, thrombosis, platelet disorders, stroke, burns, trauma, pancreatitis, diabetes, disseminated intravascular coagulation, thromboembolism, Alzheimer's disease, vascular dementia, Down's syndrome and amyotrophic lateral sclerosis.

MAO inhibitors can be linked to antiinflammatory drugs by various methods, for example a NSAID can be linked to a MAO inhibitor of the propargylamine type with the general formula (1) to form an amide bond

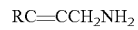

RC≡CCH$_2$NH$_2$ (1)

Where R is a hydrogen, alkyl [CH$_3$CH$_2$]$_n$ and n is an integer from 1-20, aryl, alkyl aryl group or alkoxy or aryloxy group and salts there of and other monoamine oxidase (MAO A and B) inhibitors containing a propargyl group. In cases where the MAO inhibitors do not have a free amino group available, as in the case of deprenyl, clorgyline or pargyline, a free amino group is introduced at the at the propyl carbon by arts known in the literature. The antiinflammatory drug can be selected from a group of compounds containing a free carboxyl group (—COOH) such as aspirin, genistic acid, indomethacin, ibuprofen, ketoprofen, flubioprofen, diclofenac, meclofenamic acid, fenoprofen, oxaprocin, etodolac, and other antiinflammatory drugs to which a —COOH group can be attached. The MAO inhibitor can also be attached to the antiinflammatory drugs by other methods known in the literature. Various salts, derivatives and metabolites of MAO inhibitors and antiinflammatory drugs are also contemplated in the invention.

Compounds of the invention with one or more asymmetric carbon atoms may exist as enantiomeres, diastereomers or as racemic mixtures, it is to be understood that the present invention anticipates and includes within its scope such isomers and mixtures of antiinflammatory drugs and MAO inhibitors.

The MAO inhibitors co-administered with antiinflammatory drugs used in the compositions of the invention can be any of the compounds known to the art, including those exemplified below. First, despite the introduction of several new NSAIDS, aspirin, introduced about 100 years ago is still the most widely used anti-inflammatory, analgesic, and antipyretic agent and is the standard for comparing the activities of other NSAIDS. Other salicylates used in addition to aspirin (acetylsalicylic acid) are; diflurophenyl derivatives, salicylsalicylic acid, sodium salicylate, salicyclamide, sodium thiosalicylate, choline salicylate, magnesium salicylate, choline-magnesium salicylate.

Another group of NSAID drugs included are the pyrazolon derivatives like phenylbutazone, oxyphenylbutazone, antipyrine, aminopyrine and apazone.

Another group of compounds contemplated by the invention include indomethacin, and related compounds like sulindac.

Another class of NSAIDS is the para-aminophenol derivatives (coal-tar analgesics) including phenacetin and its active metabolite acetaminophen.

Another group of NSAIDS contemplated include fenmates, which are derivatives of N-phenylanthranilic acid. Representative compounds of this group are mefenamic, meclofenamic, flufenamic, mefenomic and ectofenamic used either as the acid or as pharmaceutically acceptable salts.

Another NSAID contemplated in the invention is tolmectin.

Another class of NSAIDS is the propionic acid derivates such as ibuprofen, naproxen, flurbioprofen, fenoprofen, ketoprofen, fenbufen, pirprofen, oxaprozin and indoprofen.

Other drugs contemplated include enolic acid derivatives such as piroxicam, amperoxicam, and oxicam.

Other compounds contemplated are tenoxicam, tenidap, diclophenac, etodolac, and nabumentone.

Another group of compounds contemplated include diclofenac and diflunisal.

Another group of NSAIDS contemplated include biarylamines and derivatives.

Another contemplated group of NSAIDS are selective COX-2 inhibitors (coxibs) such as celecoxib, rofecoxib and valdecoxib. Also included are nitric oxide-releasing NSAIDS and Nitric oxide-generating NSAIDS, nitrate-containing NSAIDS, agents that stimulate nitric oxide, or inhibit phosphodiesterases.

The compositions of the invention also include NSAIDS to which MAO inhibitors have been attached.

Each of the above-contemplated NSAIDS is described in more detail in the literature such as in Goodman and Gilman, The Pharmaceutical Basis of Therapeutics ($8^{th}$ Edition, McGraw-Hill, 1993, pages 638-681; and Physians Desk Reference, 2001.

Monoamine oxidase inhibitors contemplated in the invention include both reversible and irreversible MAO-A and MAO-B inhibitors. Examples of such compounds are 1-deprenyl [R-(−)deprenyl or selegiline], d-deprenyl [S-(+)-deprenyl, clorgyline, pargyline, iproniazid, nialamide, phenelzine, tranylcypromine, quinacrine, hydrazine, carboxamide, RO 16-6491 [N-(2-Aminoethyl-4-chlorobenzamide)], RO 41-1049 [N-(2-aminoethyl-5-3fluorophenyl thiazolecarboxamide)], propargylamines (e.g.; lazabemide, rasagiline), N-propargylamine compounds, N-methyl-propargylamine and N-methyl-N-(2-pentyl)-propargylamine. Other MAO inhibitors contemplated include various synthetic and natural preparations with MAO inhibitor activity.

Other antiinflammatory drugs contemplated include glucocorticoids, acetaminophen, lipoxygenase inhibitors, phosphodiesterase inhibitors, statins, estrogens, androgens, leukotriene antagonists, angiotensin conerting enzyme inhibitors, dual-action compounds, and combinations of these drugs with other agents.

Chemical modifications, derivatives and metabolites of antiinflammatory drugs and MAO inhibitors are also contemplated in the invention.

These and other objects of the invention are provided in the claims.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

Details of the invention are described in terms of NSAIDS, but similar effects are anticipated for other anti-inflammatory drugs.

DESCRIPTION OF PREFERRED
EMBODIMENTS

It has been discovered, surprisingly, that MAO-A or MAO-B inhibitors such as 1-deprenyl display new modes of action which are totally unrelated to their mechanism of action as selective inhibitors of MAO-A and or MAO-B or other previously reported actions of these compounds. For example, it has been found that MAO-A or MAO-B inhibitors such as 1-deprenyl reduce the gastrointestinal toxicity of NSAIDS like aspirin and indomethacin. The MAO inhibitor can be administered along with the NSAID or can be attached to the NSAID molecule as described. It was also found that the MAO inhibitors reversed the gastrointestinal damage induced by NSAIDS. The MAO inhibitors also will prevent and/or reverse gastrointestinal ulcers produced by stress or *helicobacter pylori* infection. The MAO inhibitor will similarly reduce the renal, platelet and other toxicities of NSAIDS and other anti-inflammatory drugs.

It has also been found that MAO inhibitors did not reduce the analgesic activity of NSAIDS. It has been observed that the use of MAO inhibitors along with NSAIDS did not reduce the anti-inflammatory activity of NSAIDS. So addition of MAO inhibitor did not adversely affect the therapeutic efficacy of NSAIDS.

The protective effect of MAO-A and MAO-B inhibitors against toxic effects induced by NSAIDS and their ability to provide tissue protection may be mediated by a number of actions exerted by MAO inhibitors. These actions may include the following: antioxidant property, free radical scavenging, inhibition of oxidative stress, antiapoptotic activity, anti-inflammatory action, enhanced expression and activity of antioxidant enzymes, endothelial protection, neuroprotection, vasodilation, enhanced blood flow, stimulation of constitutive neuronal and endothelial nitric oxide synthase leading to increased production of nitric oxide, inhibition of platelet activation, and antiatherogenic activity.

Thus a combination of NSAIDS and MAO inhibitors can be used for a variety of disorders including neuronal and peripheral tissues for which NSAIDS have been shown to be effective. Various NSAIDS and MAO inhibitors previously listed can be used for such purposes.

The discovery of the previously unknown effects of 1-deprenyl and other MAO-A or MAO-B inhibitors leads directly to a method of protecting the gastrointestinal tract and other tissues from the toxic side effects of NSAIDS. The present inventor has demonstrated that NSAIDS cause gastrointestinal damage. NSAID-mediated GI damage is considered to be a major factor leading to the high morbidity and mortality rates associated with NSAID use. Administration of MAO inhibitors or MAO inhibitors attached to NSAIDS can prevent and reverse the toxic effects of NSAIDS and provide tissue protection, thus permitting the safe and prolonged use of NSAIDS for the treatment of a number of disorders.

The ability of 1-deprenyl and other MAO-A or MAO-B inhibitors to prevent and reverse GI damage caused by NSAIDS has been confirmed by studies with rat stomachs. The ability of MAO inhibitors not to interfere with and reduce the analgesic and antiinlammatory activities of NSAIDS also has been confirmed with animal experiments.

It is postulated that the cytoprotective effect of MAO inhibitors in preventing and/or reversing the NSAID toxicity may be mediated by a combination of several cytoprotective actions of these compounds listed previously.

For the purposes of the invention the term "therapeutically effective amount" refers to the amount of the MAO inhibitor which is capable of producing the intended action. While individual requirements vary, determination of ideal ranges for effective quantities of each MAO inhibitor is within the skill of the art. The dosage required to provide an effective amount of the composition can be determined by one with ordinary skill in the art and this composition will vary, depending on the medical condition, physical status, sex, weight, nature and extent of the disease of the recipient, and frequency of treatment.

The dosage of any NSAID which will be effective in the treatment of a particular disorder or condition will depend on the nature of the disorder or condition, and can be determined by standard clinical procedures, as listed in the Physician's Desk Reference, Medical Economics Company Inc; Ordell. N.J.: 2001 and other standard reference materials. The precise dose to be used in the formulation will depend on the route of administration, condition of the recipient, nature of the disease, and should be determined according to the judgement of the practitioner and each patient's individual needs.

The amount of MAO inhibitor in a pharmaceutical composition may be in the amounts of 0.1 to 10 times the molar equivalent of the NSAID. The usual daily doses of NSAIDS are 3-40 mg/kg body weight and the doses of MAO inhibitors in the pharmaceutical composition may be in the amounts of 0.1-500 mg/kg body weight daily and more usually about 0.1-50 mg/kg. Effective doses may be extrapolated from dose-response curves derived from in vitro or animal model test systems and are in the same ranges or less than as described for the commercially available compounds in the Physician's Desk Reference. Metabolites and derivatives of the compounds of the compositions are also contemplated for such application.

The invention also provides a pharmaceutical pack or kit comprising one or more containers filled with one or more of the ingredients of the pharmaceutical compositions of the invention.

The compounds of the preparation can be prepared and administered in a wide variety of oral and parenteral dosage forms. Thus the compounds of the present invention can be administered by injection, that is intravenously, intramuscularly, intracutaneously, subcutaneously, intraduodenally, or intraperetoneally. Also the compounds of the present invention can be administered by inhalation, for example intranasally. Additionally, the compounds of the present invention can be administered transdermally. It will be obvious to those skilled in the art that the following dosage forms may comprise the active components, NSAIDS and MAO inhibitors or corresponding pharmaceutically acceptable salts of the components.

For preparing pharmaceutical compositions from the compounds of the invention, pharmaceutically acceptable carriers can be either solid or liquid. Solid form preparations include powders, tablets, pills, capsules, cachets, suppositories, and dispersible granules. A solid carrier can be one or more substance, which may also act as diluents, flavoring agents, binders, preservatives, tablet disintegrating agents, or an encapsulating material.

The pharmaceutical preparation is preferably in unit dosage form. In such form the preparation is subdivided into unit dosage forms such as capsule, tablet, cachet, lozenge, powders, vials or ampules.

The compositions of this invention can further include conventional excipients, i.e.; pharmaceutically acceptable organic or inorganic carrier substances suitable for parenteral application which do not adversely react with the active compounds of the preparation.

Various delivery systems can be used to administer the therapeutic composition, e.g.; encapsulation in liposomes, microparticles, microcapsules, slow release formulations and aerosols.

The following examples illustrate various actions of MAO inhibitors either alone or in combination with NSAIDS, but do not limit the scope of the invention in any way. Further aspects and variations of the invention, based on the disclosure above and the following examples; will be apparent to the person of ordinary skill in the art.

EXAMPLE 1

Method for Attaching MAO Inhibitor to NSAID

The detailed procedure for attaching the MAO inhibitor of the propargylamine type to NSAIDS can be carried out as follows. One mol each of the propargylamine and the NSAIDS are dissolved in 100 ml dichloromethane and mixed along with 1 mol of dicyclohexyl carbodiimide (DCC). The reaction is allowed to continue for 6 hours at room temperature under stirring. At the end of the reaction, the precipitate is dried using rotary evaporation. The reaction product (amide) is separated from any unreacted starting materials by thin layer chromatography using chloroform: ethylacetate mixture (1:1). The product is scrapped off the silica column and suspended in dichloromethane and centrifuged. The supernatant is dried in a rotary evaporator. The residue is dissolved in ethanol prior to use and diluted with the appropriate solvent to produce the desired concentration. This method is suitable for NSAIDS containing a free carboxyl group (—COOH) such as aspirin, gentisic acid, indomethacin, ibuprofen, ketoprofen, flurbioprofen, diclofenac, meclofenamic acid, fenoprofen, oxaprocin, etodolac. For those NSAIDS not containing a —COOH group, it can be introduced by arts known in the literature.

EXAMPLE 2

Comparison of Analgesic Activity of NSAIDS and NSAID-MAO Inhibitor Combinations

The analgesic activity of test compounds was measured by the phenylbenzoquinone-induced writhing test in mice as described by Siegmund et al. (1957). Male C57 mice weighing 25-30 g were deprived of food overnight. Solvent or the test compounds were administered by oral gavage 1 hour prior to intraperitoneal (i.p.) injection of 2 mg/kg of phenylbenzoquinone. The MAO inhibitor was administered immediately before the NSAID. Five minutes after the i.p. injection of phenylbenzoquinone, the number of writhes during a 5-minute period was counted for each test animal. All the NSAIDS tested showed significant analgesic activity (table 1). MAO inhibitors did not diminish the analgesic activity of NSAIDS.

EXAMPLE 3

Inhibition of Leukocyte and Platelet Activation by Deprenyl

The in vivo activation of leukocytes (monocytes and neutrophyls) and platelets was studied as described by Thomas (2003). Activation and adhesion of leukocytes induced by TNF alpha was inhibited by pretreatment with 5 mg/kg of deprenyl. Similarly activation and aggregation of platelets was also inhibited by deprenyl. This clearly demonstrates anti-inflammatory and antithrombotic actions of deprenyl.

EXAMPLE 4

Comparison of the Anti-Inflammatory Activities of NSAIDS and NSAID-MAO Inhibitor Combinations The antinflammatory activities of test compounds were determined by the rat paw edema test according to the method of Winter et al; (1962). Male Sprague-Dawley rats weighing 150-250 g were deprived of food overnight. The solvent or test compounds were administered by oral gavage one hour prior to the subplantar injection of 25 microliters of 0.5% suspension of carrageenin in the right paw. The initial volume of the paw was measured immediately after carrageenin injection. The paw volume was measured again 4 hours after the injection by changes in water displacement. The MAO inhibitor 1-deprenyl by itself had no effect on paw edema. NSAIDS significantly reduced the paw edema (table 2). Addition of the MAO inhibitor 1-deprenyl (100 mg/kg) did not reduce the anti-inflammatory activity produced by 250 mg/kg of aspirin. Thus the MAO inhibitor did not have an adverse effect on the anti-inflammatory activity of NSAIDS.

EXAMPLE 5

Effect of MAO Inhibitor on NSAID-Induced Gastric Lesion

The rat gastric lesion test as described previously (Kitagawa et al; 1990 and Al-ghamdi et al; 1991) was used to examine the ability of test compounds to produce gastric lesion. Male Sprague-Dawley rats weighing 250-300 g were deprived of food for 24 hours, with free access to water and then dosed by oral gavage with solvent or drugs given at a volume of 0.5 ml/100 g body weight. For the unmodified NSAIDS being given in combination with a MAO inhibitor, the MAO inhibitor was administered by oral gavage immediately prior to the administration of NSAID by oral gavage. Food was withheld for 8 hours after the initial dosing. For acute studies, rats were euthenized by carbon dioxide, 8 hours after dosing and the stomachs were dissected. For modified NSAIDS with attached MAO inhibitors, the compounds were administered by oral gavage, food was withheld for 8 hours, animals were euthanized and the stomachs were examined for the presence of lesions. For investigating the reversal of NSAID induced gastric lesion, following 8 hours after NSAID dosing the animals were provided food and water ad libitum. They were treated daily with oral gavage of MAO inhibitor for 7 days. These animals were then euthanized and the stomachs examined for the presence of lesions. After euthenazing, the stomachs were dissected along the greater curvature, rinsed with saline to remove the debris, the cleaned tissue was pinned open in a dish, covered with saline and examined for hemorrhagic lesions. Gastric lesions per mm were calculated by adding the lesions in the observed area. The tissue was also photographed under microscope to evaluate the extent of gastric lesions. The NSAIDS produced significant gastrointestinal lesion (table 3). Pretreatment with 1-deprenyl provided protection against the NSAID induced gastric lesion. The NSAID attached to the MAO inhibitor also attenuated the gastric toxicity of NSAIDS. The gastric lesions were also reversed by daily administration of 1-deprenyl for 7 days. The ability of MAO inhibitors to protect the gastrointestinal tissue from cytotoxic damage is clearly demonstrated.

EXAMPLE 6

Effect of MAO Inhibitor on the Inflammatory Mediators C-Reactive Protein

C-reactive protein (CRP) is a marker of inflammation, particularly cardiovascular disease. CRP levels are also elevated in obesity, diabetes, and may be a side effect of hormone replacement therapy. Reduction of CRP levels by drugs provide protection against these conditions. Blood samples were drawn from adult human subjects before and after oral administration of 1-deprenyl. The CRP levels were measured by immunoassay as described by Ridker (2001). Oral administration of 10 mg of 1-deprenyl for one week produced a 30% reduction in blood level of CRP.

TABLE 1

Analgesic activities of test compounds

| Compound (mg/kg) | Analgesic activity |
| --- | --- |
| Aspirin (200) | +++ |
| Indomethacin (200) | +++ |
| Aspirin (200) + 1-deprenyl (100) | +++ |
| Indomethacin(200) + 1-deprenyl (100) | +++ |
| Aspirin-Propargylamine (200) | +++ |

+++ indicates 90-100% analgesic activity.

TABLE 2

Anti-inflammatory activities of test compounds

| Compound (mg/kg) | Antiinflammatory activity (% swelling) |
|---|---|
| Control (carageenin only) | 100 |
| Aspirin (250) | 54 |
| Aspirin (250) + 1-deprenyl (100) | 56 |
| Aspirin-Propargylamine (250) | 52 |

TABLE 3

Effect of test compounds on NSAID-induced gastric lesion

| Compound (mg/kg) | Relative gastric lesion |
|---|---|
| Aspirin (250) | ++++ |
| Indomethacin (250) | ++++ |
| Ibuprofen (250) | +++ |
| Aspirin (250) + 1-deprenyl (100) | ++ |
| Aspirin (250) + 1-deprenyl (200) | + |
| Indomethacin (250) + 1-deprenyl (200) | + |
| Aspirin-Propargylamine (250) | ++ |
| Indomethacin-Propargylamine (250) | ++ |
| Ibuprofen-Propargylamine (250) | ++ |
| Aspirin (250) + 1-deprenyl (100) for 7 days | ++ |

100% of the gastric lesion produced by the NSAID ++++
61-80% of the gastric lesion produced by the NSAID +++
21-40% of the gastric lesion produced by the NSAID ++
1-20% of the gastric lesion produced by the NSAID +

Discussion

The results of these examples clearly indicate that, under the conditions tested, the monoamine oxidase inhibitor compounds and compositions protect against gastrointestinal, renal and other toxicities induced by nonsteroidal anti-inflammatory drugs and provide tissue protection through a variety of biological actions. Therapeutic methods of using the MAO inhibitors and nonsteroidal anti-inflammatory drugs for the treatment of inflammatory disorders, pain, fever, gastrointestinal lesions and a variety of cardiac, cerebral and peripheral disorders are disclosed. Similar protective effects against toxicity of other anti-inflammatory drugs are also contemplated.

The ratio of MAO inhibitors and NSAIDS used for these applications can be varied depending on the nature and severity of the disorder, and the affected tissue or organ.

Having now fully described the invention, it will be appreciated by those skilled in the art that the same can be performed within a wide range of equivalent parameters, concentrations and conditions without departing from the spirit and scope of the invention and without undue experimentation.

While the invention has been described in detail with respect to particular preferred embodiments, it should be understood that such description is presented by way of illustration and not limitation. Many changes and modifications within the scope of the present invention may be made without departing from the spirit thereof, and the invention includes all such modifications.

All references cited herein, including journal articles or abstracts, published or corresponding U.S. or foreign applications, issue U.S. or foreign patents, or any other references are entirely incorporated by references herein, including all data, tables, figures, and text presented in the cited references. Additionally, the entire contents of the references cited within the references cited herein are also entirely incorporated by references.

Reference to known methods steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not limitation, such that the terminology or phraseology of the present specification is to be interpreted by the skilled artisan in light of the teachings and guidance presented herein, in combination with knowledge of one of ordinary skill in the art.

REFERENCES

Al-ghamadi et al. J. Int. Med. Res. 19: 2242 (1991)
Brikmayer et al. J. Neur. Transm. 64: 113-127 (1985).
Carillo et al. Life Sci. 67: 577-585 (2000)
Catella-Lawson et al. N. Engl. J. Med. 345: 1801-1808 (2001)
Dycek Le. et al. Drug Metabolism and Disposition. 29: 1156-1161 (2001)
Emery, Am. J. Med. 100 (1A): 425-455 (2001)
Finnerty B M. Postgraduate Med. 110: 87-94, (2001)
Fored et al. N. Engl. J. Med. 345: 1809-1817 (2001)
Glavin G B. Neurosci. Letters 70: 379-381 (1986)
Graumlich J E. Postgrad. Med. 109: 117-128 (2001)
Gupta R A et al. Nature Reviews Cancer 1: 11-21 (2001)
Hennan et al. Circulation 104: 820-825 (200).
In'T Veld et al. New. Engl. J. Med. 345: 1515-1521 (2001)
Kitagawa et al. J. Pharmacol. Exp. Ther. 253: 1133-1137 (1990)
Knoll et al. Adv. Biochem. Psychopharmacol. 5: 3939-3408 (1972)
Knoll et al. Life Sci. 45: 525-531 (1989)
Lanas A. I. Am. J. Med. 110/1A: 705-735 (2001)
Lauer M S. N. Engl. J. Med. 346: 1468-1474 (2002)
Mizuta I. Biochem. Biophys. Res. Comm. 279: 751-755 (2000)
Mukherjee et al. JAMA 286: 954-959 (2001)
Patrono C. Am. J. Med. 110/1A: 62S-65S (2001)
Rocha G M. et al. PNAS 98: 5317-5322 (2001)
Siegmund et al. Proc. Soc. Exp. Biol. Med. 95: 729-731 (1957)
Shih, Neuropsychopharmacology 4: 1-7 (1991).
Surronen et al. Biochem. Pharmacol. 59: 1589-1595 (2000)
Thomas T. et al. NeuroReport 9: 2595-2600 (1998)
Thomas T. Neurobiol. Aging 21: 343-348 (2000)
Thomas T. et al. NeuroReport 12: 3263-3267 (2001)
Thomas T. et al. Exp. Clin. Endocrinol. And Diabetes 11: 8-11, (2003)
Thomas T. et al. Climacteric 6: 293-301 (2003)
Thyagarajan et al. J. Neuroimmunology 109: 95-104 (2000)
Wallace et al. Thrombosis Res. 93: 43-50 (1999)
Wallace J L, and Soldato P D. Fundamental and Clin. Pharmacol. 17: 11-20 (2003)
Winter et al. Proc. Soc. Exp. Biol. Med. 111: 544-547 (1962)
Wolfe et al. N. Engl. J. Med. 340: 1888-1899 (1999)

Weggen S. et al. Nature 414: 212-216 (2001)
Yeomans N D. Am. J. Medicine 10/1A: 245-285 (2001)

What is claimed is:

1. A method of reducing and reversing the gastrointestinal ulceration effects of anti-inflammatory drugs and enhancing the beneficial effects of anti-inflammatory drugs, comprising:
   administering to a subject an effective amount of monoamine oxidase inhibitor;
   wherein the anti-inflammatory drug and monoamine oxidase inhibitor are chemically linked, physically mixed or administered separately.

2. A method according to claim 1, wherein said anti-inflammatory drug is selected from a group consisting of nonsteroidal anti-inflammatory drugs, steroids, cyclooxygenase-3 inhibitors, 5- lipoxygenase inhibitors, leukotriene receptor antagonists, leukotriene A4 hydrolase inhibitors, antihistaminics, histamine 2 receptor antagonists, phosphodiesterase-4 antagonists, cytokine antagonists, CD44 antagonists, 3-hydroxy-3-methylglutaryl coenzyme A inhibitors, statins, thiazolidinediones, combinations of these drugs with other agents, derivatives and metabolites of antiinflammatory agents.

3. A method according to claim 2, wherein said non-steroidal anti-inflammatory drugs is selected from a group consisting of nonspecific cyclooxygenase inhibitor, cyclooxygenase-1 inhibitor, cyclooxygenase-2 inhibitor, metabolites, and derivatives thereof.

4. A method according to claim 1, wherein said monoamine oxidase inhibitor is selected from the group consisting of monoamine oxidase-A inhibitors, monoamine oxidase-B inhibitors, l-deprenyl, R— (-)deprenyl, d-deprenyl [S-(+)-deprenyl], acetylenic tryptamine derivatives, clorgyline, pargyline, iproniazid, nialamide, phenelzine, tranylcypromine, quinacrine, hydrazine, carboxamide, RO 16-6491 [N-(2-Aminoethyl-chlorobenzamide)], RO 41-1049 [N-(2-aminoethyl-5-3fluorophenyl thiazolecarboxamide)], propargylamines (e.g.; lazabemide, rasagiline), N-propargylamine compounds (N-methyl propargylamine and N-methyl-N-(2 pentyl)-propargylamine), and derivatives and metabolites thereof,.

5. A method according to claim 1, wherein the antiinflammatory drug toxicity is ameliorated by the cytoprotective actions of monoamine oxidase inhibitors comprising of monoamine oxidase inhibition, neuroprotection, endothelial protection, antiinflammatory action, antiplatelet action, anti-atherogenic action, inhibition of activation and migration of leukocytes, decreasing the levels inflammatory markers, antioxidant action, free radical scavenging, antiapoptotic action, reduction of hypoxia, reduction of oxidative stress, antagonism of cytotoxic actions of toxic agents, inhibition of tumor growth, vasodilation, increased blood flow, enhanced expression of antioxidant enzymes and growth factors, stimulation of constitutive nitric oxide synthase enzymes resulting in the enhanced production of nitric oxide, and inhibition of cytochrome P450 enzymes.

6. A method according to claim 1, wherein the monoamine oxidase inhibitors is linked to non-steroidal anti-inflammatory drugs by covalently linking a non-steroidal anti-inflammatory drugs to a monoamine oxidase inhibitor to form an amide bond
   wherein the monoamine oxidase inhibitor is a propargylamine, deprenyl with an amino group introduced at the —NCH$_3$ group to form —NCH$_2$NH$_2$, clorgyline with a free amino group introduced at the —NCH$_3$ group to form —NCH$_2$NH$_2$, pargyline with a free amino group introduced at the —NCH$_3$ group to form —NCH$_2$NH$_2$, and monoamine oxidase inhibitors having formula (1):

$$RC\!\!=\!\!CCH2NH2 \qquad (1)$$

where R is a hydrogen, alkyl, aryl, alkyl aryl group, [CH$_3$ CH$_2$]n where n is an integer from 1-20, alkoxy group, aryloxy group, monoamnine oxidase inhibitors containing a propargyl group and salts thereof;
   wherein the non-steroidal anti-inflammatory drugs is be selected from a group of compounds containing a free carboxyl group (—COOH) and
   where the amino group of the propargylamine, the NH2 group of the monoamine oxidase inhibitor, or the —NCH$_2$NH$_2$ of the deprenyl or clorgyline is directly linked to the non-steroidal anti-inflammatory drugs to form an amide bond.

* * * * *